United States Patent
Panek, Jr. et al.

(10) Patent No.: US 8,684,176 B2
(45) Date of Patent: Apr. 1, 2014

(54) APPARATUS AND METHOD FOR UNWINDING A NEEDLE PORTION

(75) Inventors: Robert Joseph Panek, Jr., Huntley, IL (US); John C. Japuntich, Woodstock, IL (US); James A. Arendt, Elk Grove Village, IL (US)

(73) Assignee: Covidien LP, Mansfield, MA (US)

( * ) Notice: Subject to any disclaimer, the term of this patent is extended or adjusted under 35 U.S.C. 154(b) by 202 days.

(21) Appl. No.: 12/986,344

(22) Filed: Jan. 7, 2011

(65) Prior Publication Data

US 2011/0100850 A1 May 5, 2011

Related U.S. Application Data

(60) Continuation of application No. 12/332,894, filed on Dec. 11, 2008, now Pat. No. 7,877,849, which is a division of application No. 10/632,877, filed on Aug. 1, 2003, now abandoned, which is a division of application No. 09/934,298, filed on Aug. 21, 2001, now Pat. No. 6,712,207.

(51) Int. Cl.
*B65D 83/10* (2006.01)

(52) U.S. Cl.
USPC ........... 206/366; 206/363; 206/365; 29/426.1

(58) Field of Classification Search
USPC .................. 29/426.1, 801; 206/363–366
See application file for complete search history.

(56) References Cited

U.S. PATENT DOCUMENTS

| | | |
|---|---|---|
| 4,466,538 A | 8/1984 | Gianni |
| 4,488,643 A | 12/1984 | Pepper |
| 4,494,652 A | 1/1985 | Nelson et al. |
| 4,576,281 A | 3/1986 | Kirksey |
| 4,801,013 A | 1/1989 | Bruno |
| 4,986,811 A | 1/1991 | Thead et al. |
| 4,989,307 A | 2/1991 | Sharpe et al. |
| 4,995,871 A | 2/1991 | Sasaki et al. |
| 5,069,667 A | 12/1991 | Freundlich et al. |
| 5,092,462 A * | 3/1992 | Sagstetter et al. ............ 206/366 |
| 5,188,598 A | 2/1993 | Thead et al. |
| 5,201,417 A | 4/1993 | Outlaw, III |
| 5,273,161 A * | 12/1993 | Sagstetter .................... 206/366 |
| 5,322,164 A | 6/1994 | Richardson et al. |
| 5,409,112 A | 4/1995 | Sagstetter |
| 5,409,113 A | 4/1995 | Richardson et al. |
| 5,474,181 A | 12/1995 | Shillington et al. |

(Continued)

OTHER PUBLICATIONS

Office action issued Dec. 19, 2005 in related U.S. Appl. No. 10/721,388 now issued as Patent No. 7,243,792—9 pgs.

(Continued)

*Primary Examiner* — David Bryant
*Assistant Examiner* — Christopher M Koehler
(74) *Attorney, Agent, or Firm* — Lisa E. Winsor, Esq.

(57) ABSTRACT

A container system is provided for removing a needle portion from a needle holder of a needle system. The system includes a receptacle defining an opening, a lid configured to cover the receptacle opening, wherein the lid defines an aperture having a shape configured to receive a needle system having a first configuration. The system also includes an adapter configured for engagement in the lid aperture, wherein the adapter defines an aperture having a shape configured to receive a needle system having a second configuration, and wherein the engagement of the adapter in the lid aperture resists rotation of the adapter with respect to the lid.

11 Claims, 13 Drawing Sheets

(56) References Cited

U.S. PATENT DOCUMENTS

| | | | | |
|---|---|---|---|---|
| 5,573,113 | A | * | 11/1996 | Shillington et al. .......... 206/366 |
| 5,857,569 | A | | 1/1999 | Hoftman et al. |
| 6,027,392 | A | | 2/2000 | Ruhlman |
| 6,062,001 | A | | 5/2000 | Kunik |
| 6,158,314 | A | * | 12/2000 | Thead et al. ....................... 83/23 |
| 6,247,592 | B1 | * | 6/2001 | Racicot et al. ................. 206/366 |
| 6,253,916 | B1 | | 7/2001 | Bickel |
| 6,474,472 | B1 | * | 11/2002 | Shaw ............................ 206/366 |
| 6,691,867 | B1 | * | 2/2004 | Bickel et al. ................... 206/366 |
| 6,712,207 | B2 | * | 3/2004 | Panek et al. .................... 206/366 |
| 7,243,792 | B2 | * | 7/2007 | Panek et al. .................... 206/366 |
| 2003/0038046 | A1 | * | 2/2003 | Panek, Jr. et al. .............. 206/366 |
| 2003/0183546 | A1 | * | 10/2003 | Crawford ...................... 206/366 |
| 2004/0099555 | A1 | * | 5/2004 | Panek et al. .................... 206/366 |

OTHER PUBLICATIONS

Response filed Jun. 16, 2006 to Office Action dated Dec. 19, 2005 regarding related U.S. Appl. No. 10/721,388 now issued as Patent No. 7,243,792—10 pgs.

Office action issued Sep. 1, 2006 in related U.S. Appl. No. 10/721,388 now issued as Patent No. 7,243,792—5 pgs.

Response filed Jan. 29, 2007 to Office Action dated Sep. 1, 2006 regarding related U.S. Appl. No. 10/721,388 now issued as Patent No. 7,243,792—8 pgs.

Office action issued Jul. 24, 2008 in related U.S. Appl. No. 10/632,877 now Abandoned—8 pgs.

Response filed Aug. 20, 2008 to Office Action dated Jul. 24, 2008 regarding related U.S. Appl. No. 10/632,877 now Abandoned- 2 pgs.

Office action issued Nov. 24, 2008 in related U.S. Appl. No. 10/632,877 now Abandoned—7 pgs.

Response filed Feb. 18, 2009 to Office Action dated Nov. 24, 2008 regarding related U.S. Appl. No. 10/632,877 now Abandoned—7 pgs.

Office action issued Jun. 8, 2009 in related U.S. Appl. No. 10/632,877 now Abandoned—7 pgs.

Office action issued Mar. 25, 2010 in related U.S. Appl. No. 12/332,894 now issued as Patent No. 7,877,849—11 pgs.

Response filed Aug. 19, 2010 to Office Action dated Mar. 25, 2010 regarding related U.S. Appl. No. 12/332,894 now issued as Patent No. 7,877,849—17 pgs.

* cited by examiner

APPARATUS AND METHOD FOR UNWINDING A NEEDLE PORTION

CROSS REFERENCE TO RELATED APPLICATIONS

This application is a continuation of U.S. patent application Ser. No. 12/322,894, filed Dec. 11, 2008, now U.S. Pat. No. 7,877,849, which is a divisional of U.S. patent application Ser. No. 10/632,877, filed Aug. 1, 2003, now abandoned, which is a divisional of U.S. patent application Ser. No. 09/934,298, filed Aug. 21, 2001, now U.S. Pat. No. 6,712,207 issued Mar. 30, 2004, the disclosures of each of which are expressly incorporated herein by reference.

FIELD OF THE INVENTION

The present invention relates to an apparatus and method for unwinding a needle portion. More specifically, the invention relates to an adapter configured to unwind a needle portion from a needle holder so that the needle can be deposited in a disposal container.

BACKGROUND OF THE INVENTION

Due to concerns regarding contamination and injury, it is desirable to have a safe and simple method of disposing used medical needles (e.g. syringes, sharps). Emphasis has been placed on designing containers (e.g. phlebotomy disposal containers) that isolate the previously disposed needles from the medical professional that uses the container. Further, efforts have been made to provide a disposal container which a medical professional can operate easily and conveniently.

A typical needle disposal system is illustrated in FIG. 1 and is described in U.S. Pat. No. 5,322,164 issued to Richardson et al., which is incorporated herein by reference for its teachings related to needle disposal systems. The disposal container 2 shown in FIG. 1 includes a container body 4 and a lid 6. The lid 6 includes a skirt 8 which may be used to engage a top flange of container body 4 (not shown).

It is desirable to insert a used needle through an opening in the lid so that the used needle may be dropped into the container body 4 through the opening. Accordingly, lid 6 includes a first aperture 10 and a second aperture 12. Aperture 10 may be covered by a pivotal closure 14, and aperture 12 may be covered by a pivotal closure 16. Pivotal closures 14 and 16 may be joined by a bridge 18 so that they may be operated in tandem. Aperture 10 is sized larger than aperture 12. With pivotal closure 14 open, medical waste that fits through aperture 10 is simply deposited through aperture 10 and drops into container body 4.

Aperture 12 is specifically sized to receive a needle system 19, which is also illustrated in FIG. 1 and described by Richardson et al. in U.S. Pat. No. 5,322,164. Needle system 19 includes a needle holder 22 and a needle 26. Needle holder 22 includes a lower opening (not shown) that receives and retains needle 26. In order to retain the needle 26 using the lower opening, needle holder 22 includes two spring loaded side locks 24. When side locks 24 are depressed inwardly, the lower opening expands. When side locks 24 are not depressed inwardly, as shown in FIG. 1, the lower opening is in a retracted position. When the lower opening (not shown) is in the expanded position, needle 26 separates from needle holder 22. When the lower opening is in the retracted position, needle 26 is retained by needle holder 22. Aperture 12 includes tapered sides (not shown) which receive a lower portion of the outer wall 23 of needle holder 22. As needle 26 is guided into aperture 12, the tapered sides (not shown) contact and depress side locks 24, so that the lower opening expands and needle 26 is separated from needle holder 22. Needle 26 drops into container body 4, and needle holder 22 is retained or discarded in an appropriate manner.

Lid 6 also defines needle detaching device 20 adjacent to aperture 12. Needle detaching device 20 may be used to unscrew needles which are threaded to a needle holder.

While the disposal system illustrated in FIG. 1 provides an effective disposal system for certain medical waste, it does not efficiently accommodate every type of needle system in use. Particularly, many unwinding type needle systems can not be unwound and discarded by using the system illustrated in FIG. 1. An unwinding type needle system typically includes a needle and a needle holder, often threaded together. In order to dispose of a needle of an unwinding type needle system, the needle is preferably unwound from the needle holder so that the needle may drop into an accompanying disposal container.

Aperture 12 is not configured to unwind a needle from every configuration of needle holder. For example, while needle detaching device 20 may be used to unwind some types of needles from some types of needle holders, it can not accommodate every type of needle system which requires unwinding for disposal.

As such, medical professionals are often forced to choose one needle system and a corresponding disposal system over another type of system, or alternatively medical professionals stock numerous types of needle systems and disposal systems (resulting in higher costs). Accordingly, there remains a need for a disposal system that can accommodate more than one type of needle holder system.

SUMMARY OF THE INVENTION

According to one aspect of this invention, an apparatus is provided for adapting a disposal container with an opening having a first configuration for use with a needle system having a second configuration. Specifically, in a preferred embodiment, the invention provides an adapter to be inserted into an aperture of a disposal container lid, so that the container may be used to unwind needles from needle systems with varying configurations.

DETAILED DESCRIPTION OF THE DRAWINGS

Figure 1:
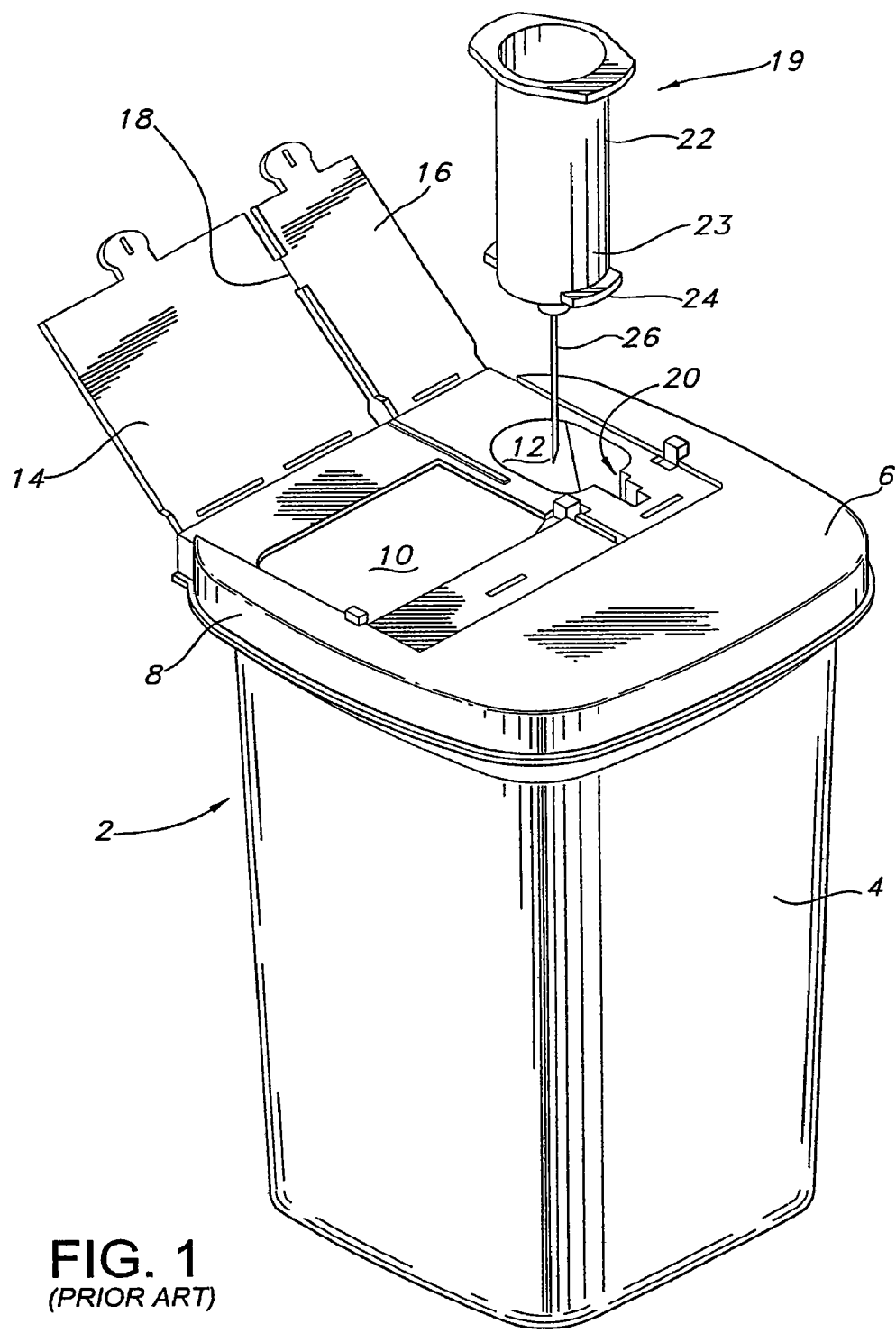
FIG. 1 is a perspective view of a prior art needle disposal system.

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose for illustration. The invention is not limited to any particular dimensions, materials, or other details of the illustrated embodiments.

Referring generally to FIGS. 2-13, a container system is provided for removing a needle portion from a needle holder 64 of a needle system. The container system includes a receptacle (similar to container body 4 illustrated in FIG. 1) defining an opening and a lid 30 configured to cover the opening of the receptacle. The lid 30 defines an aperture 38 having a shape configured to receive a needle system having a first configuration. The container system also includes an adapter 50 that is configured for engagement in lid aperture 38. The adapter 50 defines an aperture 52 having a shape configured to receive a needle system having a second configuration. The adapter 50 is engaged within the lid aperture 38 such that rotation of the adapter 50 with respect to said lid 38 is resisted.

Figure 2:
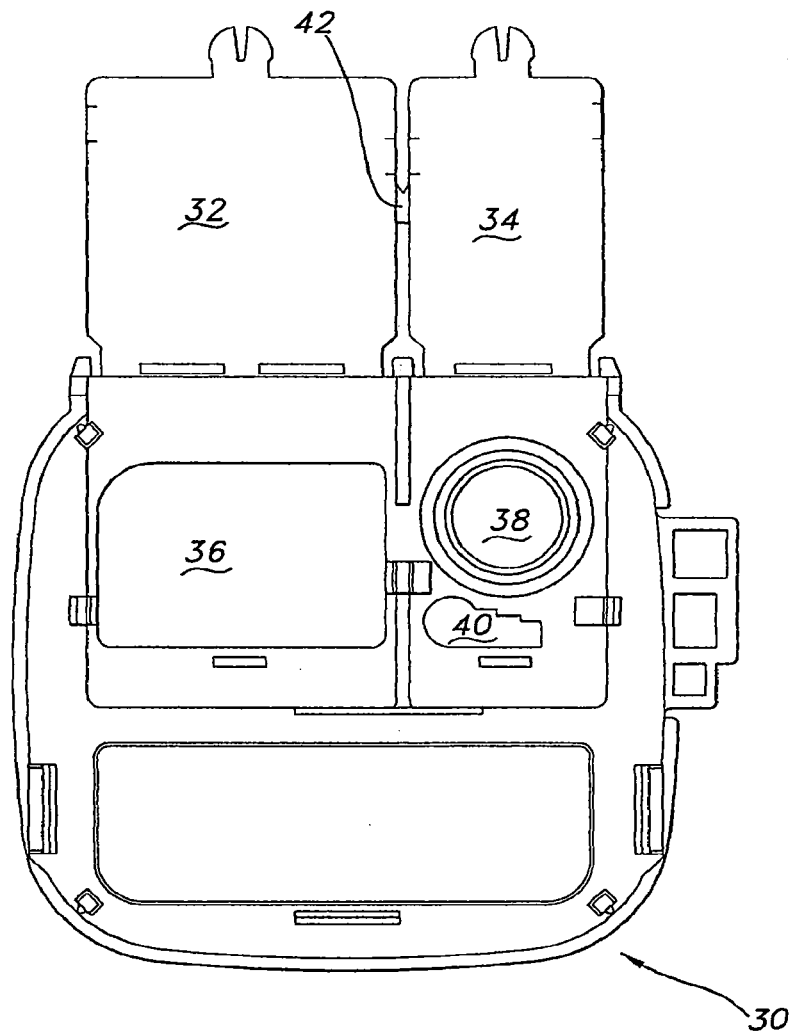
FIG. 2 is a top view of an embodiment of a lid adapted for use with a disposal container in accordance with an exemplary embodiment of the present invention.

In an exemplary embodiment of the present invention, FIG. 2 provides an illustration of a top view of a lid 30 which can be used as an alternative to the prior art lid 6 shown in FIG. 1. Lid 30 shown in FIG. 2 includes an aperture 36 and a funnel-shaped aperture 38. Aperture 36 can be covered by a pivotal closure 32, and a funnel-shaped aperture 38 can be covered by a pivotal closure 34. A Bridge 42 may be provided, connecting pivotal closures 32 and 34, such that pivotal closures 32 and 34 may be operated in tandem. Lid 30 also includes needle detaching device 40, which can be used to unwind various types of needle systems.

Medical waste, such as used needles, can be discarded by opening pivotal closure 32 and depositing the waste into the disposal container 2 through aperture 36. The discarded waste will drop into a container body attached to lid 30, similar to container body 4, shown in FIG. 1.

Needle detaching device 40 can be used to unwind various needle systems that utilize unwinding for their disposal. For example, various needle systems may include a needle holder and a needle portion. Often, the needle portion includes a needle and a protective sheath made of plastic or the like; however, the needle portion may include a needle alone. The needle holder and the needle portion may be connected by threading a threaded portion of one of the elements into a receiving threaded portion of the other element. For example, the needle portion may include a threaded male end, and the needle holder may include a threaded female end. As such, to connect the needle holder and the needle portion, the needle portion is threaded to the needle holder. After using the needle system to draw blood or the like, the needle portion is preferably unwound from the needle holder in order to dispose of the needle portion. This can be accomplished by inserting the needle portion of the needle system into the needle detaching device 40 and rotating the needle holder until the needle portion separates from the needle holder and drops into the container body.

Figure 3:
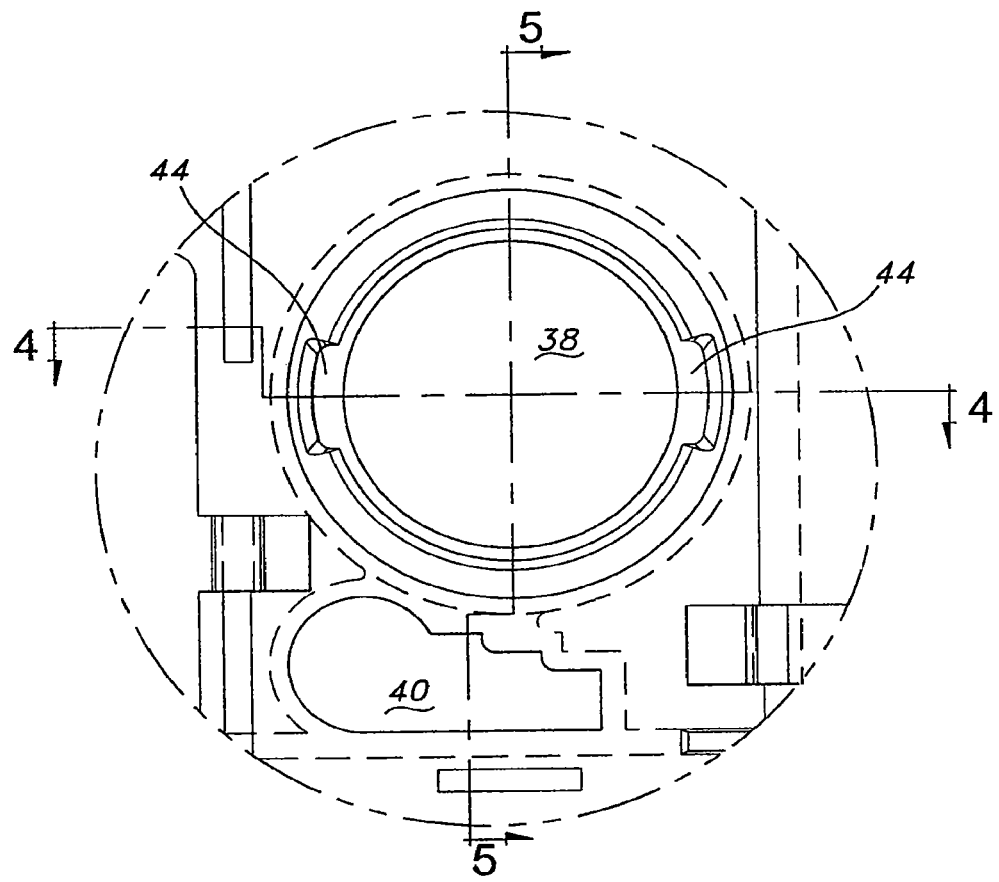
FIG. 3 is a partial top view of the lid shown in FIG. 2.

FIG. 3 provides a partial top view of lid 30 and illustrates needle detaching device 40 and funnel shaped aperture 38 in greater detail. In the exemplary embodiment shown in FIG. 3, funnel-shaped aperture 38 includes a pair of depressions 44. The functionality of depressions 44 will be explained below. Although FIG. 3 shows two depressions 44, this is simply an example of a number of depressions that could be included in the funnel-shaped aperture 38. It is understood that a single depression, or three or more depressions, could alternatively be included in funnel-shaped aperture 38.

Figure 4:
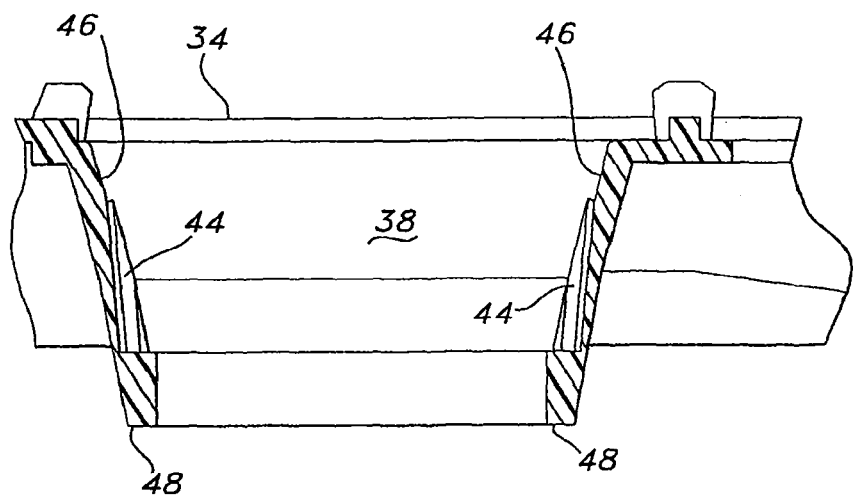
FIG. 4 is a cross sectional side view of an embodiment of an aperture included in the lid shown in FIG. 2.

FIG. 4 provides a cross sectional side view of funnel-shaped aperture 38. Pivotal closure 34 is shown covering funnel-shaped aperture 38. Funnel-shaped aperture 38 includes a tapered inside wall 46 which extends to bottom edge 48. The pair of depressions 44, which are recesses formed in inside wall 46, are also shown in FIG. 4. Although the aperture 38 is described as being substantially funnel-shaped, the aperture 38 could have a different shape such as a cylindrical shape or a square shape or a wide variety of alternative shapes.

Figure 5:
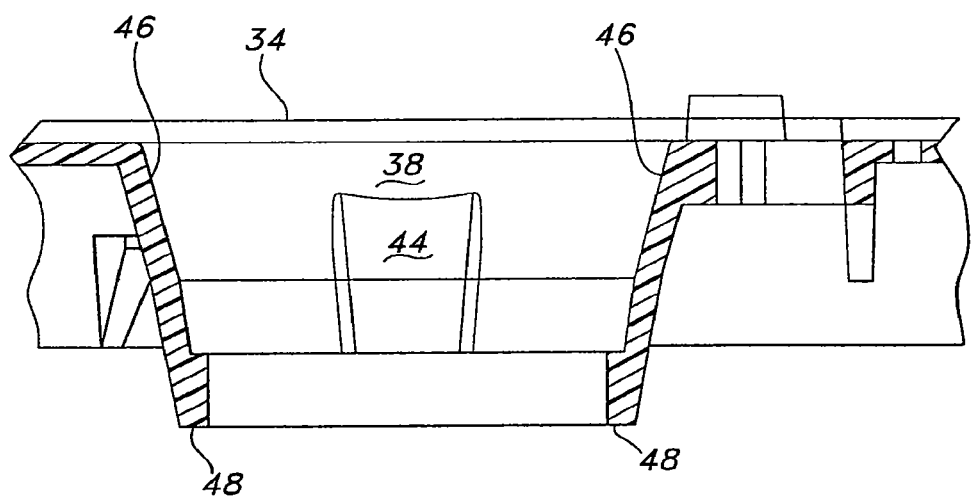
FIG. 5 is another cross sectional side view of the aperture shown in FIG. 4.

FIG. 5 provides an additional cross sectional side view of funnel-shaped aperture 38 that is perpendicular to the view shown in FIG. 4. Again, pivotal closure 34 is shown covering funnel-shaped aperture 38. Also, inside wall 46 is shown extending to bottom edge 48. A front view of depression 44, as opposed to the side view provided in FIG. 4, is also included in FIG. 5.

Figure 6:
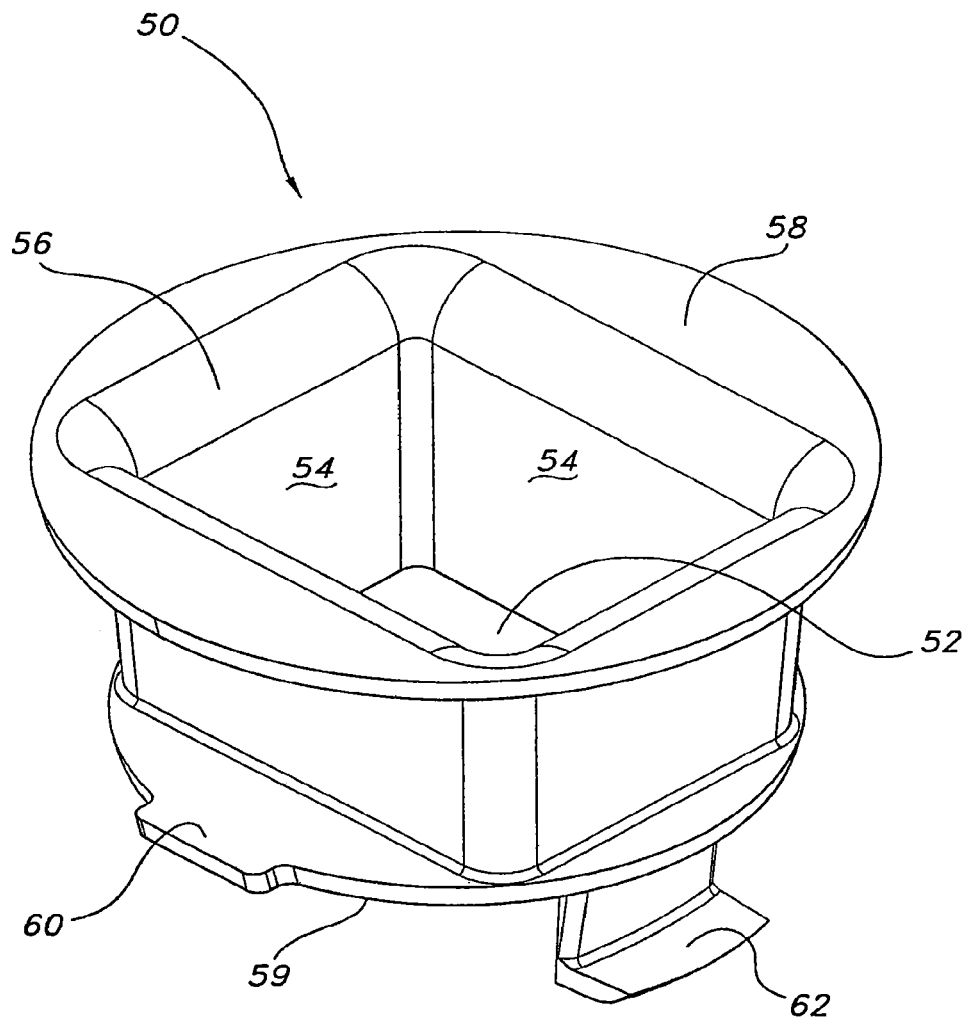
FIG. 6 is a perspective view of and embodiment of an adapter in accordance with an exemplary embodiment of the present invention.

As explained above, needle detaching device 40 nor aperture 38, shown in FIGS. 2 and 3, can accommodate every type of needle system that uses an unwinding disposal system. Therefore, as shown in FIG. 6, an exemplary embodiment of the present invention provides an adapter 50 that can be inserted into funnel-shaped aperture 38 of lid 30. As explained above, aperture 38 is not necessarily funnel-shaped, but should simply be able to accommodate an adapter 50. By using the adapter, alternative needle systems can be unwound, as will be explained below. Therefore, a single disposal container with lid 30 can be used to discard needle systems having either a configuration that can be accommodated by the aperture formed in the lid (e.g., aperture 38) or (2) a configuration that can be accommodated by the aperture formed in the adapter (e.g., aperture 52).

As shown in the perspective view of an exemplary adapter 50 provided in FIG. 6, adapter 50 includes an upper edge 58 and a lower edge 59. Upper edge 58 extends through a beveled edge 56, and into side walls 54. Side walls 54 extend to the lower edge 59. Side walls 54 define a rectangular-shaped aperture 52, which can be used to unwind needle systems which are accommodated by a rectangular aperture. Although the shape of adapter 50 is defined in FIG. 6 by upper edge 58, beveled edge 56, side walls 54, and lower edge 59, this is only an example of an adapter shape. Adapter 50 could take on any number of shapes so long as the adapter 50 can be accommodated within a lid aperture such as, for example, aperture 38. For example, adapter 50 could have a funnel-shaped exterior surface that would match the tapered shape of funnel-shaped aperture 38.

Lower edge 59 includes a pair of detents 60 (only a single detent 60 is visible from the perspective view in FIG. 6). Although lower edge 59 includes two detents 60, this is simply an exemplary embodiment, and a single detent 60, or three or more detents 60, could alternatively be included. When adapter 50 is inserted into funnel-shaped aperture 38, each detent 60 is received by a depression 44 included in funnel-shaped aperture 38. The engagement of detents 60 and depressions 44 results in a resistance to rotation of the adapter 50 within funnel-shaped aperture 38. Funnel-shaped aperture 38, illustrated in FIGS. 3 and 4, includes two depressions 44. Adapter 50, illustrated in FIG. 6, includes two detents 60. Therefore, when adapter 50 is inserted into funnel-shaped aperture 38, each detent 60 is received by a single depression 44. In an alternative embodiment, there could be more depressions 44 in funnel-shaped aperture 38 than detents 60 on adapter 50. In other words, the number of depressions 44 in the funnel-shaped opening 38 should preferably be the same or greater than the number of detents 60 on the adapter 50.

As illustrated in the exemplary embodiment included in FIG. 6, adapter 50 includes two flanges 62 (alternatively known as "feet") which extend below lower edge 59 (only a single flange 62 is visible from the perspective view in FIG. 6). When adapter 50 is inserted into funnel-shaped aperture 38 of lid 30, each flange 62 clasps around bottom edge 48 of funnel-shaped aperture 38. This engagement between flanges 62 and bottom edge 48 releasably or permanently secures adapter 50 within funnel-shaped aperture 38 and provides resistance against the removal of adapter 50 from funnel-shaped aperture 38.

Figure 7:
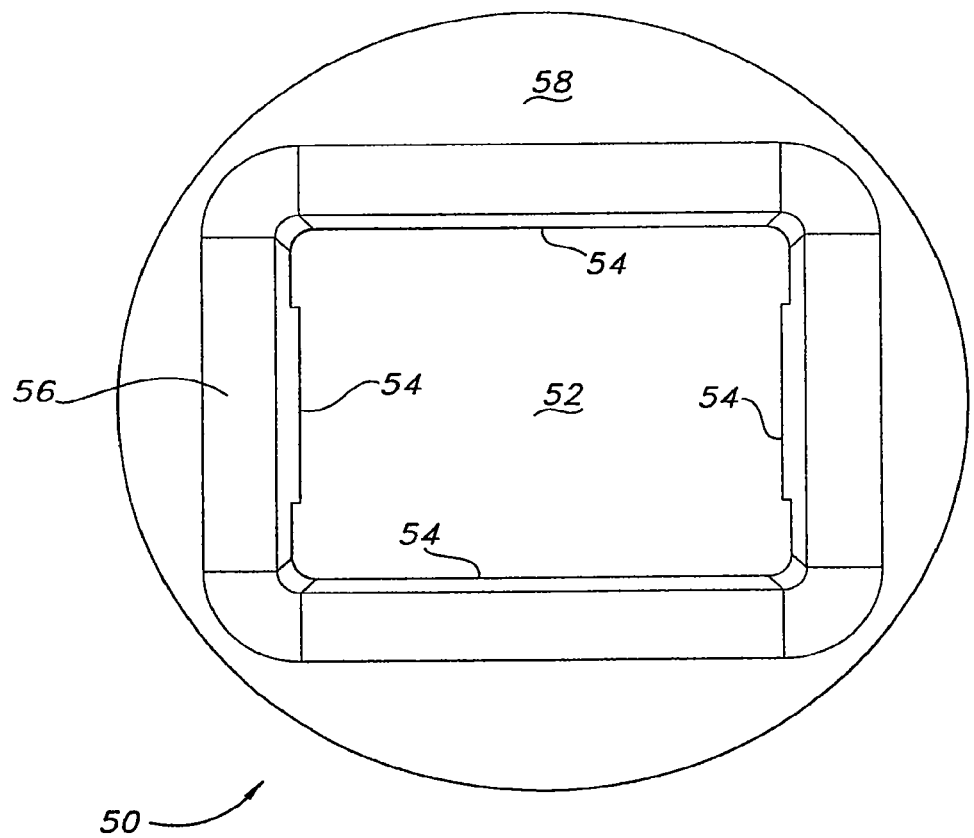
FIG. 7 is a top view of the adapter shown in FIG. 6.

FIG. 7 provides a top view of an exemplary adapter 50. As stated above, adapter 50 includes upper edge 58 which extends downward through beveled edge 56, and into side walls 54. Side walls 54 define rectangular-shaped aperture 52. Rectangular-shaped aperture 52 may be used to unwind needle systems which are accommodated by a rectangular aperture. Adapter 50 could, however, include an aperture with a shape other than a rectangular shape. For example, it may be desirable to provide a triangular-shaped or diamond-shaped aperture in the adapter 50 to accommodate differently configured needle systems, and other shapes are contemplated as well, depending upon the needle holder's configuration and design preferences.

Figure 8:
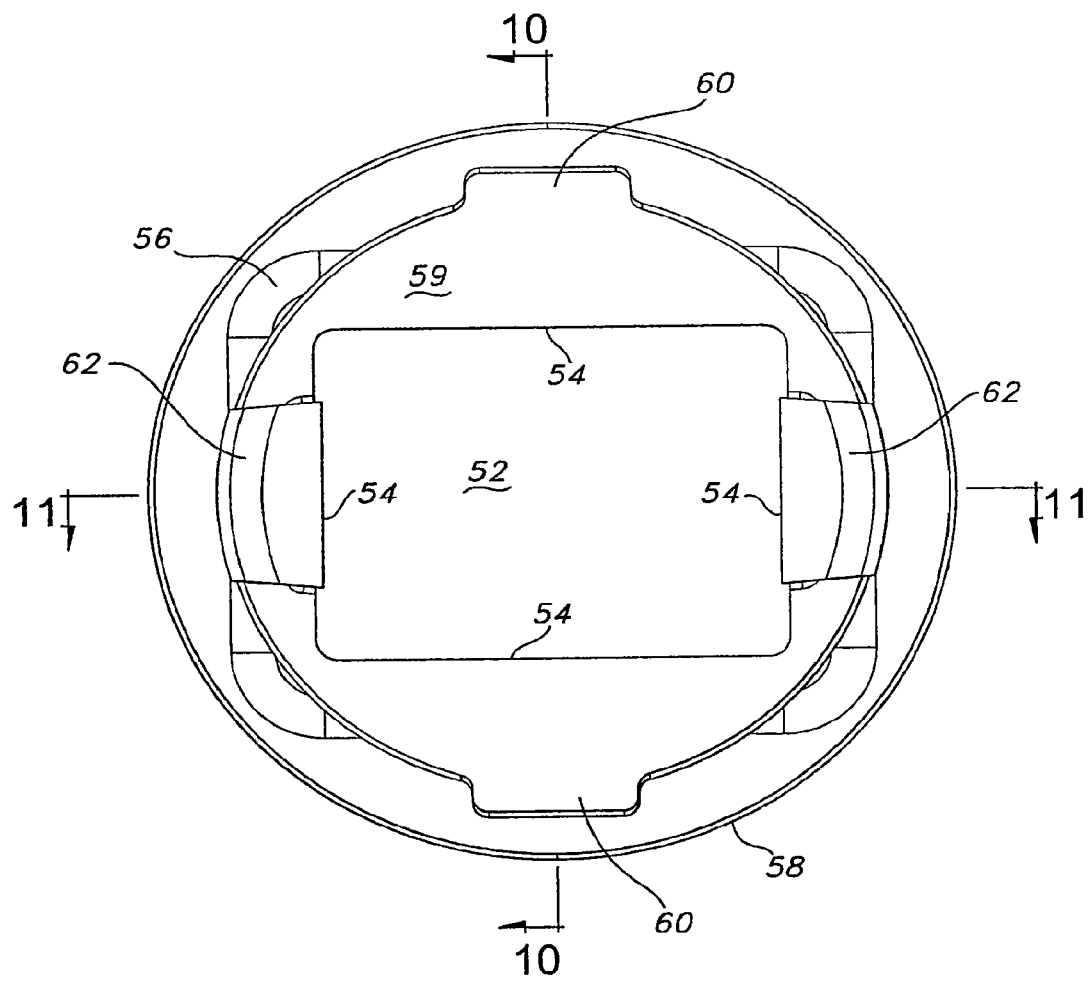
FIG. 8 is a bottom view of the adapter shown in FIG. 6.

FIG. 8 provides a bottom view of an exemplary adapter 50. Adapter 50 includes upper edge 58 which extends through beveled edge 56 into side walls 54. Side walls 54 define rectangular-shaped aperture 52. Side walls 54 extend downwardly to lower edge 59. In the exemplary embodiment shown in FIG. 8, adapter 50 includes two detents 60 that extend radially outwardly from lower edge 59, and two flanges 62 that extend downwardly from lower edge 59 and radially outwardly. When adapter 50 is inserted into funnel-shaped aperture 38 of lid 30, detents 60 of the adapter 50 are received by depressions 44 of funnel-shaped aperture 38, thereby resisting rotation of adapter 50 within funnel-shaped aperture 38. Further, upon the engagement of adapter 50 with funnel-shaped aperture 38, flanges 62 snap below and clasp around bottom edge 48 of the funnel-shaped aperture 38, thereby resisting axial removal of adapter 50 from funnel-shaped aperture 38.

Figure 9:
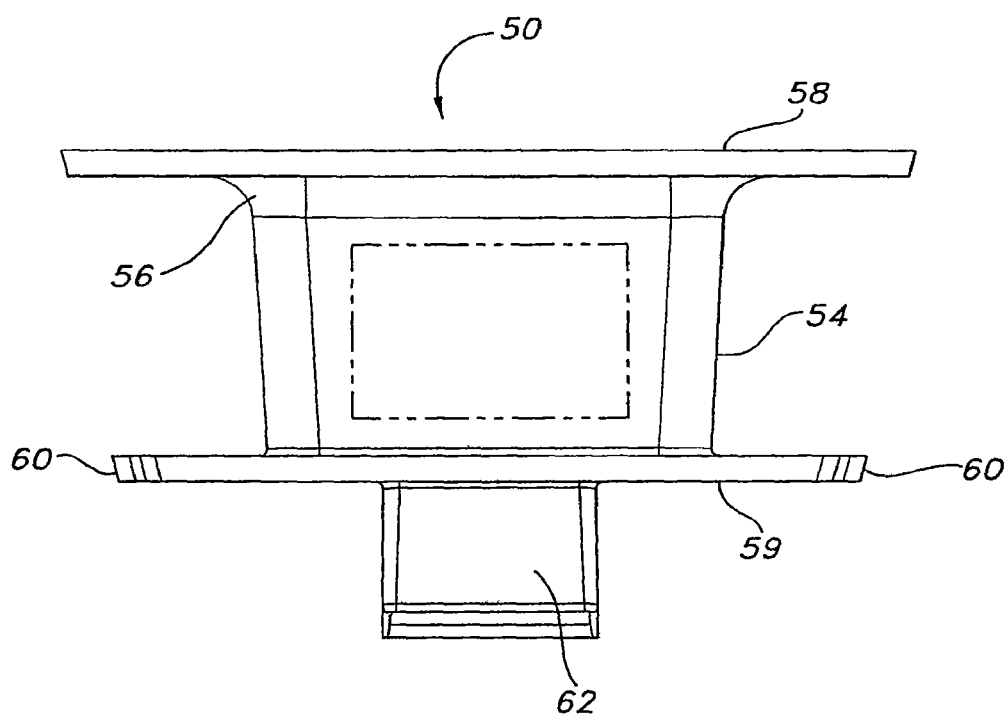
FIG. 9 is a side view of the adapter shown in FIG. 6.

FIG. 9 provides a side view of an exemplary adapter 50. Adapter 50 includes upper edge 58 which extends through beveled edge 56 into side walls 54. Side walls 54 extend downward into lower edge 59. Detents 60 extend outwardly from lower edge 59. An external view of flange 62 (only one of the two flanges 62 is visible in FIG. 9), which extends downward from lower edge 59, is also provided.

Figure 10:
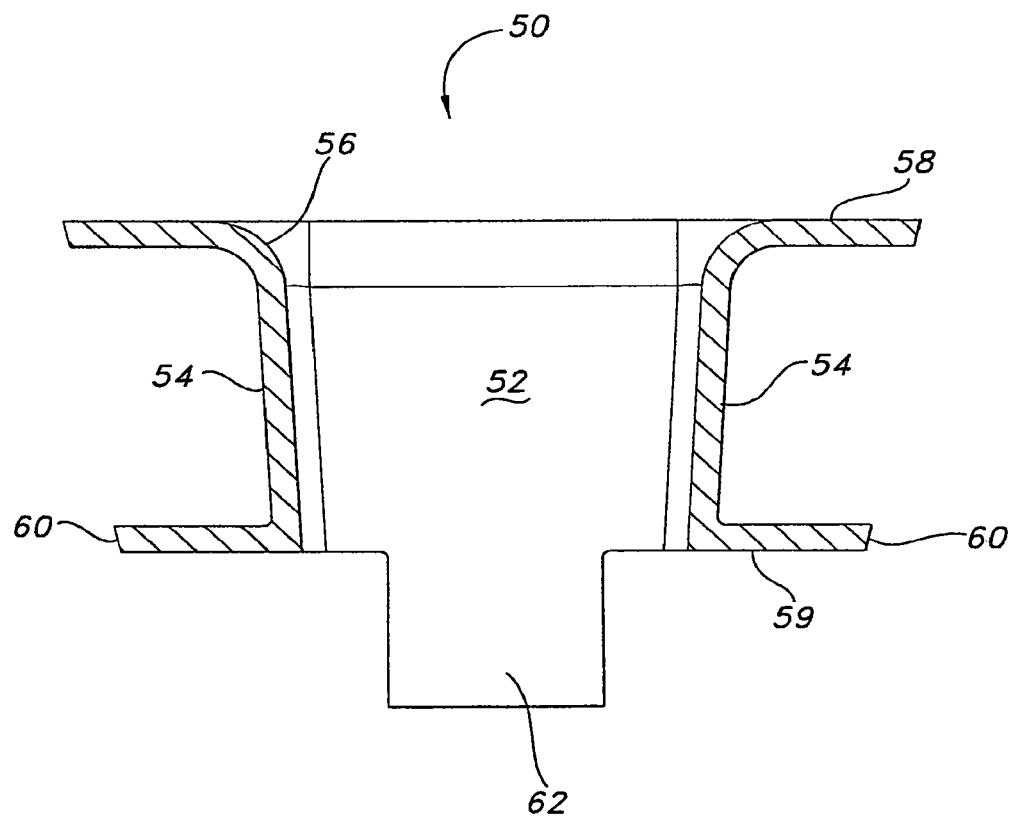
FIG. 10 is a cross sectional side view of the adapter shown in FIG. 6.

FIG. 10 provides a cross sectional view of an exemplary adapter 50. This cross sectional view illustrates the extension of upper edge 58 through beveled edge 56 and into side walls 54, and further illustrates the extension of side walls 54 to lower edge 59. Side walls 54 define rectangular-shaped aperture 52. Detents 60 extend out from lower edge 59. Also provided is an internal view of flange 62.

Figure 11:
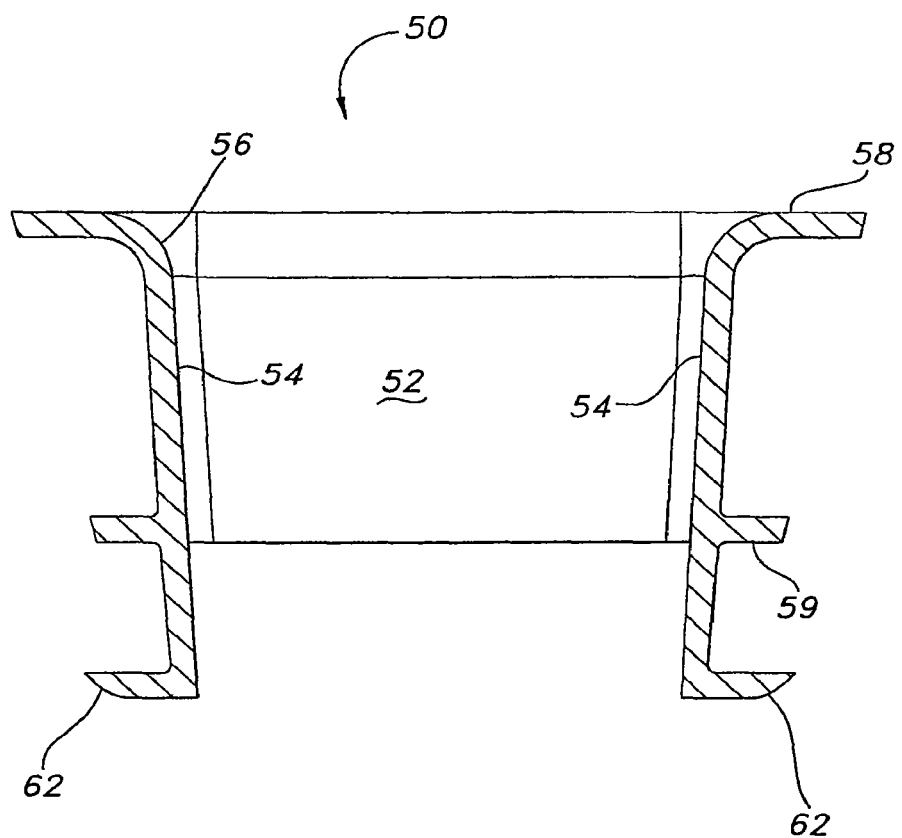
FIG. 11 is another cross sectional side view of the adapter shown in FIG. 6.

FIG. 11 provides another cross sectional view of an exemplary adapter 50. This view is perpendicular to the cross sectional view provided in FIG. 10. Again, upper edge 58 extends through beveled edge 56 into side walls 54. Side walls 54, which define rectangular-shaped aperture 52, extend downward to lower edge 59, and then further extend downward into flanges 62.

Figure 12:
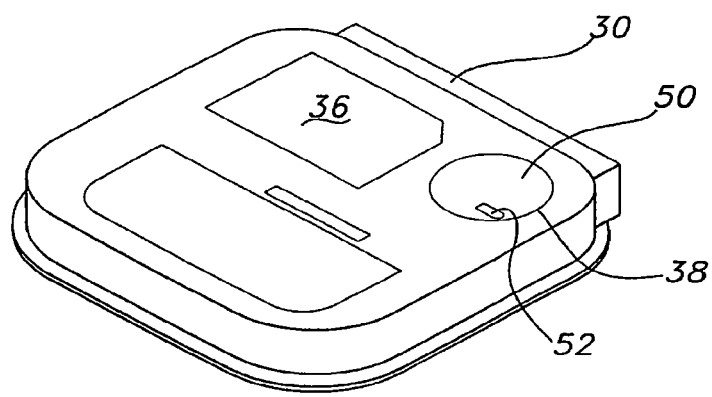
FIG. 12 is a perspective view of an embodiment of a lid for a disposal container including an adapter in accordance with an exemplary embodiment of the present invention

FIG. 12 provides a perspective view of an exemplary lid 30, with an adapter 50 engaged in the funnel-shaped aperture 38 of the lid 30. Lid 30 includes aperture 36, in addition to funnel-shaped aperture 38. Funnel-shaped aperture 38 receives adapter 50. Specifically, depressions 44 (not shown in FIG. 12) of funnel-shaped aperture 38 receive detents 60 (not shown in FIG. 12) of the adapter 50, and thereby provide resistance to rotation of adapter 50 within funnel-shaped aperture 38. Further, flanges 62 (not shown in FIG. 12) snap and clasp around bottom edge 48 (not shown in FIG. 12) of funnel-shaped aperture 38, thereby providing resistance to the removal of adapter 50 from funnel-shaped aperture 38. With adapter 50 engaged within funnel-shaped aperture 38, rectangular-shaped aperture 52 may be used to unwind needle systems that would be accommodated by the rectangular shape of aperture 52.

Figure 13:
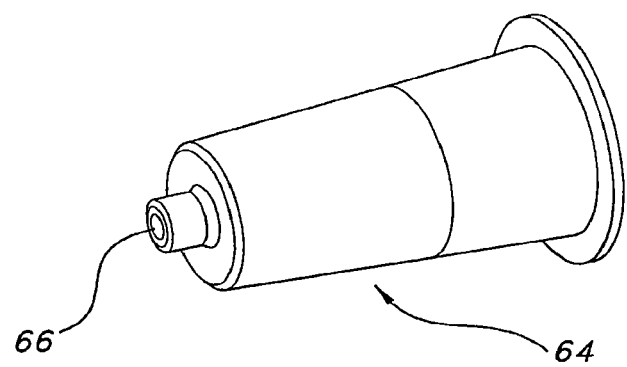
FIG. 13 is a perspective view of a needle holder that can be used in accordance with an exemplary embodiment of the present invention.

FIG. 13 provides a perspective view of an exemplary needle holder 64. Needle holder 64 and a needle portion (not shown) are included in a needle system which requires unwinding for disposal. The needle portion may include a needle and a protective sheath, or simply may include a needle alone, with no protective sheath. Needle holder 64 includes a threaded receiver 66. A needle portion (not shown) is threaded into threaded receiver 66. Although the needle portion and needle holder are engaged to one another by threading the needle portion into the threaded receiver 66, this is only an example of how the needle portion and the needle holder may be coupled. The needle system, including the needle holder 64 and the needle portion, are used for their intended medical purpose. It is then desirable to dispose of the used needle system.

The use and operation of a disposal container according to this invention will now be described. Generally, this invention makes it possible to unwind a needle portion from a needle holder of a needle system having a second configuration using a container system including a receptacle and a lid such as lid 30, wherein the lid has an aperture such as aperture 38 configured to receive a needle system having a first configuration. An adapter such as adapter 50 configured to receive the needle system having the second configuration is engaged in the lid aperture, thereby modifying the lid from being configured to receive the needle system having the first configuration to being configured to receive the needle system having the second configuration. At least a portion of the needle system having the second configuration is inserted into the adapter aperture such as the aperture 52 of the adapter 50, thereby engaging the needle portion to resist rotation of the needle portion with respect to the adapter. The needle holder is then rotated with respect to the adapter, thereby unwinding the needle portion from the needle system such that the needle portion is released into the receptacle.

More specifically, with reference to the embodiment selected for illustration in the Figures, in order to dispose of the needle system, a disposal container with a lid 30 is preferably utilized. In a preferred embodiment, lid 30 preferably includes funnel-shaped aperture 38, and adapter 50 is engaged within funnel-shaped aperture 38. In an exemplary embodiment, adapter 50 provides rectangular-shaped aperture 52. The needle portion of the needle system is inserted into rectangular-shaped aperture 52. The needle holder 64 is then rotated such that the needle portion unthreads from threaded receiver 66 of needle holder 64, and separates from the needle holder 64. The needle portion drops into the disposal container. The medical professional may then dispose of the needle holder in any approved manner, or may retain the needle holder 64 as desired.

Variations and modifications of the exemplary embodiments illustrated in the Figures can be made without departing from the scope of this invention. It should be recognized that the aperture provided in the lid of the container system can be provided with any configuration and is, therefore, not to be limited to a funnel-shaped aperture. Likewise, the adapter can be provided with an aperture having any configuration and is not to be limited to a rectangular-shaped aperture. It is preferred, however, that the configuration of the lid's aperture differs from that of the adapter's aperture in either its size or its shape. In this way, the use of the adapter in connection with a container system changes the configuration of the engagement mechanism from one configuration or size to another configuration or size. By changing the configuration of the container's engagement mechanism, for example, the adapter makes it possible to reconfigure a container system that was manufactured for use with one type or size of needle holder system for use with another type of needle holder system.

For the foregoing reasons, neither the selected configuration of the aperture in the lid nor the selected configuration of the aperture in the adapter is important to this invention. Instead, those configurations are selected based on design perameters, manufacturing techniques, cost considerations, and other factors.

Also, the nature of the means for engaging an adapter within a lid aperture is not important to this invention. Most preferably, the means for engagement between the adapter and the lid resists rotational movement of the adapter with respect to the lid and/or resists axial movement of the adapter with respect to the lid. It is recognized, however, that the means for engagement between the adapter and the lid can alternatively be configured to permit movement, perhaps both axial and rotational, between the adapter and the lid if so desired.

It will be appreciated that additional variations and modifications of the disclosed, preferred embodiments can be made without departing from the scope of this invention, which is defined separately in the appended claims.

What is claimed:

1. An adapter for use with a container system including a receptacle, and a lid having an aperture configured and dimensioned for engagement with a first needle system having a first needle configuration, the adapter comprising: structure facilitating releasable connection of the adapter with the aperture in the lid such that relative movement between the adapter and the lid is inhibited, the adapter being configured and dimensioned to modify the configuration of the aperture in the lid to facilitate engagement with a second needle system having a second, different needle configuration for detaching a needle portion of the second needle system, wherein the adapter includes side walls extending between an upper edge and a lower edge, the lower edge extending outward from the side walls, and a flange extends downward and outward from the lower edge, the flange being configured and dimensioned for engaging the aperture in the lid to inhibit removal of the adapter from the aperture in the lid.

2. The adapter of claim 1, wherein the upper edge extends through a beveled edge.

3. The adapter of claim 1, wherein the side walls define a substantially rectangular aperture.

4. The adapter of claim 1, wherein the lower edge includes at least one detent configured and dimensioned for engagement with a corresponding depression formed in the aperture in the lid.

5. The adapter of claim 4, wherein the lower edge includes a plurality of detents configured and dimensioned for engagement with a corresponding number of depressions formed in the aperture in the lid.

6. The adapter of claim 4, wherein the at least one detent extends radially outward from the lower edge.

7. The adapter of claim 1, further comprising:
   a first detent extending radially outward from the lower edge; and
   a second detent extending radially outward from the lower edge, the second detent being opposite the first detent.

8. The adapter of claim 7, wherein the flange is a first flange spaced from both the first and second detents, and the adapter further comprises a second flange extending downward and outward from the lower edge, the second flange being opposite the first flange and spaced from both the first and second detents.

9. The adapter of claim 1, wherein the flange includes a base extending downward from the lower edge and a foot extending outward from the base, the foot being adapted to engage a bottom edge of the aperture of the lid of the container system.

10. The adapter of claim 1, wherein the adapter is a one-piece structure.

11. The adapter of claim 1, wherein the flange extends downward and outward from only a portion of the lower edge.

* * * * *